(12) United States Patent
Kwak et al.

(10) Patent No.: US 8,379,211 B2
(45) Date of Patent: Feb. 19, 2013

(54) APPARATUS FOR SENSING PRECIPITATION DENSITY OF SLUDGE IN WASTE WATER TREATMENT TANK AND METHOD THEREFOR

(75) Inventors: Jung-Pil Kwak, Seoul (KR); Wook Hyeon, Seongnam-si (KR); Kyeong Sun Jeong, Gyeonggi-do (KR); Yoo Jong Kim, Gyeonggi-do (KR); Hong Soo Oh, Goyan-si (KR); Kyeong Joo Na, Seoul (KR)

(73) Assignee: Environmental Management Corporation (KR)

( * ) Notice: Subject to any disclaimer, the term of this patent is extended or adjusted under 35 U.S.C. 154(b) by 652 days.

(21) Appl. No.: 12/514,858

(22) PCT Filed: Nov. 13, 2007

(86) PCT No.: PCT/KR2007/005696
§ 371 (c)(1),
(2), (4) Date: Feb. 8, 2010

(87) PCT Pub. No.: WO2008/060087
PCT Pub. Date: May 22, 2008

(65) Prior Publication Data
US 2010/0149539 A1 Jun. 17, 2010

(30) Foreign Application Priority Data

Nov. 14, 2006 (KR) .................. 10-2006-0112280
Jan. 8, 2007 (KR) .................. 10-2007-0002160

(51) Int. Cl.
*G01N 21/59* (2006.01)
*G01N 21/15* (2006.01)

(52) U.S. Cl. .................. 356/440; 356/246

(58) Field of Classification Search .......... 356/432–442, 356/246; 73/61.49, 61.75, 61.79, 64.55; 210/202, 195.3, 611; 367/165, 191
See application file for complete search history.

(56) References Cited

U.S. PATENT DOCUMENTS

| 4,201,477 A | 5/1980 | Palmer et al. |
| 5,127,961 A * | 7/1992 | Aiton .................. 134/22.12 |

(Continued)

FOREIGN PATENT DOCUMENTS

| JP | 63256827 A | * 10/1988 |
| JP | 03-108640 A | 5/1991 |
| KR | 10-1999-0030798 A | 5/1999 |
| KR | 10-2003-0030610 A | 4/2003 |

OTHER PUBLICATIONS

"International Application Serial No. PCT/KR2007/005696, International Search Report mailed Feb. 4, 2008", 2 pgs.

(Continued)

*Primary Examiner* — Sang Nguyen
(74) *Attorney, Agent, or Firm* — Schwegman Lundberg & Woessner, P.A.

(57) ABSTRACT

The present invention relates to an apparatus for sensing precipitation density of sludge in a wastewater treatment tank, more particularly to an apparatus and method for precisely taking density of sludge precipitated in a wastewater treatment tank without being contaminated by sludge. The present invention of an apparatus for sensing precipitation density of sludge in a waste water treatment tank comprises a container which is tube-shaped with a bottom thereof open and submerged in wastewater as filled with gas therein; and a sensor which is installed in the space in the container, and senses sludge density as not directly contacting with wastewater.

19 Claims, 4 Drawing Sheets

U.S. PATENT DOCUMENTS

| | | | | |
|---|---|---|---|---|
| 5,835,454 | A | * | 11/1998 | Maltby .......................... 367/165 |
| 6,057,773 | A | * | 5/2000 | Shukla et al. ................. 340/623 |
| 6,062,070 | A | * | 5/2000 | Maltby et al. ................. 73/61.49 |
| 6,678,050 | B2 | * | 1/2004 | Pope et al. .................... 356/435 |
| 7,731,855 | B2 | * | 6/2010 | Dunbar et al. ................. 210/741 |
| 2007/0002678 | A1 | * | 1/2007 | Murakami .................... 366/116 |

OTHER PUBLICATIONS

"International Application Serial No. PCT/KR2007/005696, Written Opinion mailed Feb. 4, 2008", 3 pgs.

* cited by examiner

APPARATUS FOR SENSING PRECIPITATION DENSITY OF SLUDGE IN WASTE WATER TREATMENT TANK AND METHOD THEREFOR

RELATED APPLICATIONS

This application is a U.S. National Stage Filing under 35 U.S.C. 371 from International Patent Application Serial No. PCT/KR2007/005696, filed 13 Nov. 2007 and published on 22 May 2008 as WO 2008/060087 A1, which claims the priority benefit of Korean Application Serial No. 10-2006-0112280, filed 14 Nov. 2006 and Korean Application Serial No. 10-2007-0002160, filed 8 Jan. 2007, the contents of which are incorporated herein by reference in their entirety.

TECHNICAL FIELD

The present invention relates to an apparatus for sensing precipitation density of sludge in a wastewater treatment tank, more particularly to an apparatus and method for precisely taking density of sludge precipitated in a wastewater treatment tank without being contaminated by sludge.

BACKGROUND ART

As well known, organics in household or industrial wastewater are environment pollutants which contaminate water of rivers or lakes. Therefore, in order to reduce such water pollution, it has been regulated to release wastewater less than the Effluent Limits after being purified in a wastewater treatment system so as to lower the biological oxygen demand (BOD) as possible.

Generally, the treatment in a wastewater treatment system is divided into three steps: a first step of pre-treatment, a second step of main treatment, and a third step of phostrip process. In the first step of pre-treatment, floating solids or suspended solids are treated by a screen and precipitate flotation; in the second step of main treatment, insoluble colloids, soluble colloids, and hazardous organics (BOD, COD) are treated by coagulation & sedimentation, electrocoagulation, neutralization, filtration, activated sludge process, trickling filter process, and stabilization pond or oxidation pond; and in the third step of phostrip process, nitrogen, phosphorus, suspended solids, organics, inorganic salts, etc. are treated by denitrification, coagulation & sedimentation, filtration, diatomite, an activated carbon, evaporation, flocculation, extraction, reverse osmosis, electrodialysis, ion exchange and so on.

Such a wastewater treatment system has essentially a unit process of coagulation & sedimentation in the wastewater treatment tank in all the three steps. And most water contaminants are treated physicochemically, biochemically, and in other way; then next sedimented through flucculent settling and compression; and the sedimented contaminants are discharged to a dehydrator to be dehydrated and disposed by incineration, landfilling, or ocean dumping.

Generally, a plurality of sludge density sensors are installed at different heights in a wastewater treatment tank of a wastewater treatment system. And the lower part of a wastewater treatment tank has a sludge drawing equipment to draw sedimented sludge out when sludge density sensed by the sensor is over a given value.

The density sensors comprise a light-emitting unit to emit light, a light-receiving unit to which the light emitted from the light-emitting unit and reflected by sludge enters, and an optical sensor to measure sludge density by the intensity of the light entered in the light-receiving unit.

Conventional sludge density sensors used in wastewater treatment systems, however, measure the density in a fixed spot in a specific place of the wastewater treatment tank. Therefore, it is difficult to exactly measure the state of sludge in wastewater treatment tank on the whole. In addition, when density reverse occurs between the upper part and lower part because of stirring in the wastewater treatment tank, it results in discharging sludge on not exact density.

In addition, since the light-emitting unit and the light-receiving unit of conventional sludge density sensors are installed to contact with sludge directly in the wastewater treatment tank, the sludge grows bigger as sticked on the light-emitting unit and the light-receiving unit of sensors, thereby preventing the sensors from absorbing the light and resulting in mismeasuring the density.

Therefore, conventional sludge density sensors are to be cleaned regularly from the sludge sticked on its surface and reinstalled in the wastewater treatment tank.

The reinstallation, however, takes time because it is difficult to separate the sensor out of the wastewater treatment tank and replace, and is not so pleasant work because the installer has to stir the sludge layer to take the sensor out and reinstall it therein. In order to solve such problems, a sensor with rotating wiper on the surface of the sensing unit has been developed to do auto-cleaning in the precipitation tank, yet this sensor has also inevitable accumulation of pollution caused by long-term operation.

Besides, another method to measure sludge density is to collect and analyze precipitated sludge samples from a certain depth of a wastewater treatment tank. This method, however, takes long time to carry out and is difficult to measure the density in real time because of pollution of the collecting tube and sample container.

DISCLOSURE OF INVENTION

Technical Problem

Accordingly, the present invention has been made in view of the above problems occurring in the prior art, and it is an object of the present invention to provide an apparatus and method for sensing sludge density in a wastewater treatment tank which is capable of measuring sludge density by the water level from the upper part to lower part of a wastewater treatment tank, and sensing state of the sludge in the tank, thereby making it easy to treat the sludge.

Another object of the present invention is to provide an apparatus and method for sensing sludge density in a wastewater treatment tank which is free from pollution on the light-emitting unit and the light-receiving unit of the sensor, thereby making exact measurement of sludge density and no cleansing of the sensor possible.

Technical Solution

The above object of the present invention can be achieved by an apparatus for sensing precipitation density of sludge in a waste water treatment tank. The apparatus comprises a container which is tube-shaped with a bottom thereof open and submerged in wastewater as filled with gas therein; and a sensor which is installed in the space in the container 101, and senses sludge density as not directly contacting with wastewater.

The above object of the present invention can also be achieved by a method for sensing precipitation density of sludge in a waste water treatment tank. The method comprises steps of moving in which a density sensing unit is allowed to move by a given distance from the upper part to the lower part in a wastewater treatment tank and to stop at a measuring spot in said wastewater treatment tank; stabilizing in which said density sensing unit stands by for a set time after the time said density sensing unit stops at said measuring spot; and measuring in which said density sensing unit measures sludge density at the water level of said measuring spot after said set time is over, wherein said steps of moving, stabilizing, and measuring are sequentially repeated until said density sensing unit reaches the last measuring spot in the lower part of said wastewater treatment tank.

Advantageous Effects

The present invention has advantageous effects in that it can grasp the whole state of sludge density in a wastewater treatment tank and perform the process of discharging sludge more accurately since the sludge density sensing unit of the present invention measures accurate sludge density by water level of the wastewater treatment tank as moving up and down therein.

The present invention also has advantageous effects in that the sensor of the present invention can take sludge density with the light-emitting unit and the light-receiving unit thereof not directly contacting with sludge, thereby preventing sludge from adhering onto them. The sensor is free from contamination, so it does not have to be cleansed even after being long time used.

DESCRIPTION ON MAIN REFERENCE NUMERALS

Figure 1:
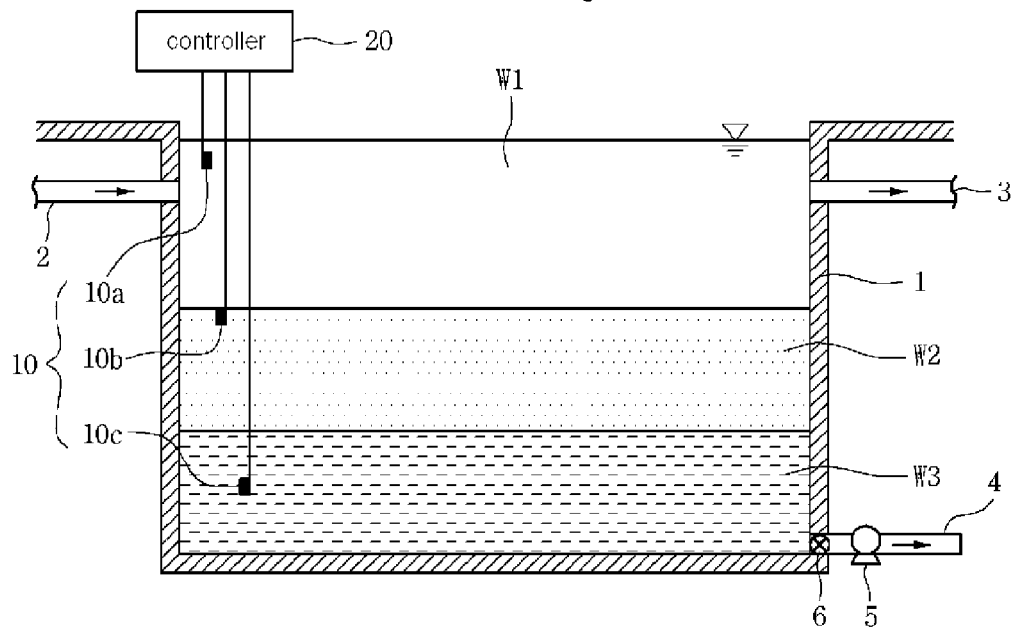
FIG. 1 is a sectional view of an embodiment of an apparatus for sensing sludge density applying a sludge density sensing unit according to the present invention.

1: wastewater treatment tank 2: influent tube 3: effluent tube
4: sludge discharging tube 5: discharging pump 6: valve
10: density sensing unit 20: controller 30: elevating unit
31: guide frame 32: upper pulley 33: lower pulley
34: belt 35: motor 101: container
102: sensor 103: light-emitting unit 104: light-receiving unit
105: gas injection tube 106: valve 107: light shielding wall
108: vibration shielding plate Mode for the Invention The terms and the words used in the specification and the claims should not be limitedly construed with ordinary or lexical meaning. Rather, they should be construed with the meanings and the conceptions according to the idea of the present invention, abiding by the principle that an inventor can properly define the conception of terms so as to describe his or her own invention with the best manner.

While the present invention has been described with reference to particular illustrative embodiments, it is not to be restricted by the embodiments but only by the appended claims. It is to be appreciated that those skilled in the art can change or modify the embodiments without departing from the scope and spirit of the present invention.

Hereinafter, the preferred embodiments of the present invention will be described in detail with reference to the accompanying drawings.

FIG. 1 is a sectional view of an embodiment of an apparatus for sensing sludge density applying a sludge density sensing unit according to the present invention. Referring to FIG. 1, a wastewater treatment tank 1 has an influent tube 2 on a side of the upper part thereof for wastewater to flow therein; an effluent tube 3 on the other side of the upper part thereof for supernatant water therein to go out; and a sludge discharging tube 4, a discharging pump 5, and a valve 6 on a side of the lower part thereof for settled sludge to be discharged out thereof.

The inside of the wastewater treatment tank 1 can be divided by the upper part of supernatant water layer W1, the middle part of sludge-floating layer W2 where not settled sludge is floating, and the lower part of sludge-settled layer W3.

In addition, the inside of the wastewater treatment tank 1 has a first density sensing unit 10a, a second density sensing unit 10b, and a third density sensing unit 10c installed to measure density of sludge, and each density sensing unit is electrically connected with a controller 20 to transfer measured value in real time.

The density sensing unit 10 takes sludge density by amount of light which enters the light-receiving unit of an optical sensor. The detail composition of the density sensing unit 10 will be described with reference with FIGS. 3 to 5.

The first density sensing unit 10a takes a role to check the degree of pollution of the supernatant water as well as to prevent measurement errors of the second and third density sensing units 10b, 10c caused by the difference of amount of light between day time and night time, which means that at day time or on a fine day the amount of light entering the light-receiving unit of the density sensing unit 10 is high, while at night time or on a cloudy day the amount of light entering the light-receiving unit of the density sensing unit 10 is low, so that there can be sludge density measurement errors by the density sensing unit 10.

The controller, therefore, corrects the measured values taken by the second and third density sensing units 10b, 10c in accordance with the amount of light measured by the first density sensing unit 10a.

Meanwhile, when the wavelength of the taken light source is within those of visible rays, the influence of a foreign light source is inevitable; when the taken light source is within infrared rays or within ultraviolet rays, the influence of a foreign light source is preventable. In addition, when a diffusion-type lamp such as a general LED or a halogen lamp is taken as a light source, not only the reflection area of the light source by means of sludge increases, but also does the reflection area on the water surface, thereby increasing the possibility for the light reflected by the mere stirring of water surface to directly enter the light-receiving unit of a sensor. Otherwise, when the light source is a laser, its high permeability and uniform direction prevent signals from diffusing out which is caused by reflection of water surface. As a result, when the light source is an infrared or ultraviolet laser, it has an advantageous effect in that it decreases the influence of a foreign light source and light diffusion caused by reflection of water surface, thereby taking exact sludge density.

Later description of an embodiment of the density sensing unit 10 takes an LED light source.

Description of the measurement of sludge density and discharging of sludge performed in the above sludge density sensing apparatus is as follows.

Wastewater which comes into the wastewater treatment tank 1 through the influent tube 2, goes through a prescribed process, and then the sludge therein sediments. At this time, the second and third density sensing units 10b, 10c take a measurement of density of the sedimented sludge in real time.

As the wastewater treatment process proceeds, more sludge sediments and the density taken by the second density sensing unit 10b increases.

When the sludge density taken by the second density sensing unit 10b is over the set value in the controller 20, the controller 20 opens the valve 6a and operates the discharging pump 5 to discharge the sludge out through the sludge discharging tube 4.

As sludge are discharged out through the sludge discharging tube 4, the height of sludge-settled layer W3 gets lower; when the sludge-settled layer W3 goes near to the lower part of the third density sensing unit 10c, the density taken by the third density sensing unit 10c drops rapidly.

Then, as the controller 20 takes the signal that the density taken by the third density sensing unit 10c is lower than the set value in therein, the valve 6 gets closed and the operation of the discharging pump 5 stops, thereby stopping the sludge discharging.

In the wastewater treatment tank 1, the density sensing and the operation of the discharging pump 5 repeatedly take place, resulting in discharging the sludge.

Figure 2:
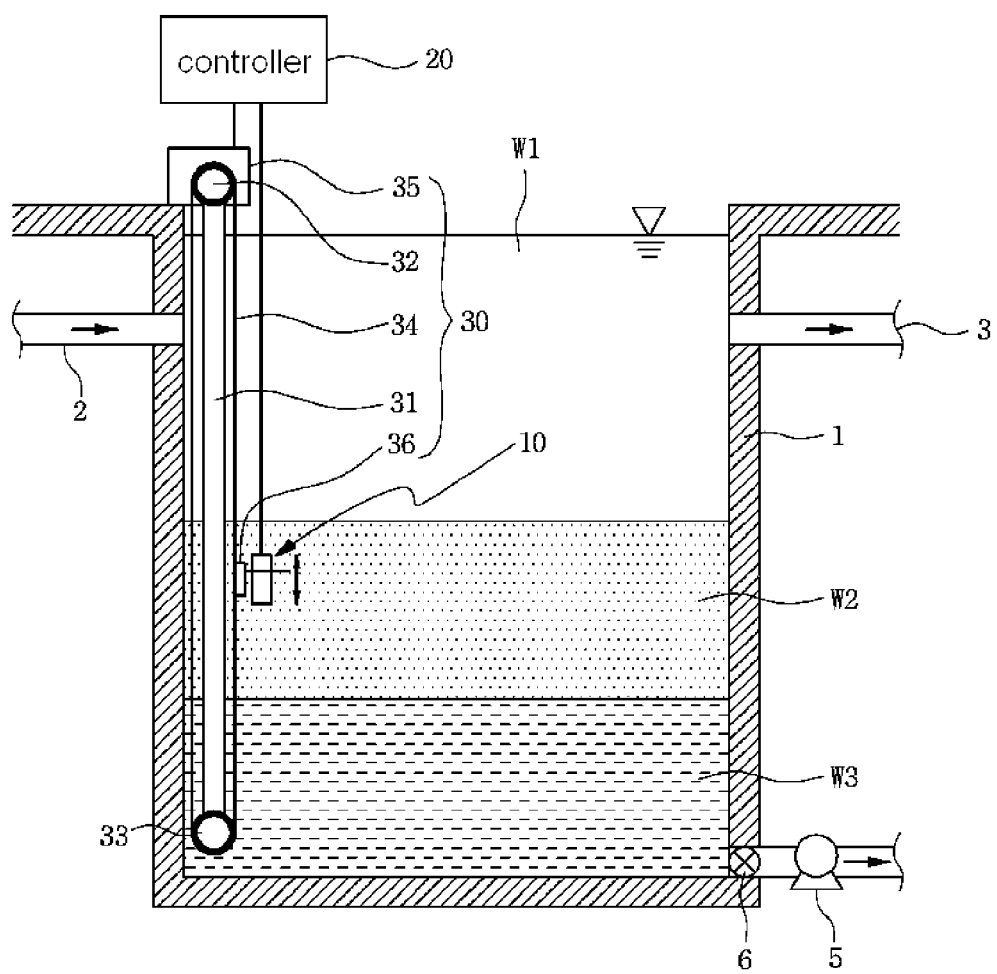
FIG. 2 is a sectional view of another embodiment of an apparatus for sensing sludge density applying a sludge density sensing unit according to the present invention.

FIG. 2 is a sectional view of another embodiment of an apparatus for sensing sludge density applying a sludge density sensing unit according to the present invention. Referring to FIG. 2, a wastewater treatment tank 1 has an influent tube 2 on a side of the upper part thereof for wastewater to flow therein; an effluent tube 3 on the other side of the upper part thereof for supernatant water therein to go out; and a sludge discharging tube 4, a discharging pump 5, and a valve 6 on a side of the lower part thereof for settled sludge to be discharged out thereof.

The inside of the wastewater treatment tank 1 can be divided by the upper part of supernatant water layer W1, the middle part of sludge-floating layer W2 where not settled sludge is floating, and the lower part of sludge-settled layer W3.

In addition, the wastewater treatment tank 1 has a density sensing unit 10 to measure density of sludge and an elevating unit 30 to moving the density sensing unit 10 up and down therealong installed in a side thereof. The density sensing unit 10 is electrically connected with a controller 20 to transfer measured value in real time.

The density sensing unit 10 takes sludge density by height of the wastewater as moving up and down along the elevating unit 30 in the wastewater treatment tank 1. At this time, the density sensing unit 10 takes sludge density by amount of light which enters the light-receiving unit of an optical sensor.

The elevating unit 30 is to move the density sensing unit 10 to any height of wastewater in the wastewater treatment tank 1. In this embodiment, the elevating unit 30 comprises a guide frame 31 installed vertically in the wastewater treatment tank 1, a upper pulley 32 and a lower pulley 33 installed at the upper part and the lower part of the guide frame 31 respectively, a belt 34 located on the upper pulley 32 and the lower pulley 33 with tension given thereon, a connection piece 36 to connect the density sensing unit 10 with the belt 34, a motor 35 to rotate the upper pulley 32 to desired degree, and an encoder (not shown) to control the moving distance of the density sensing unit 10 by sensing rotating of the motor 35.

Of course, the elevating unit 30 can be composed variously by use of other well-known linear motion devices.

Since the elevating unit 30 is submerged in the water, it is preferable to be made of corrosion proof stainless steel or a resin such as Teflon.

Figure 3:
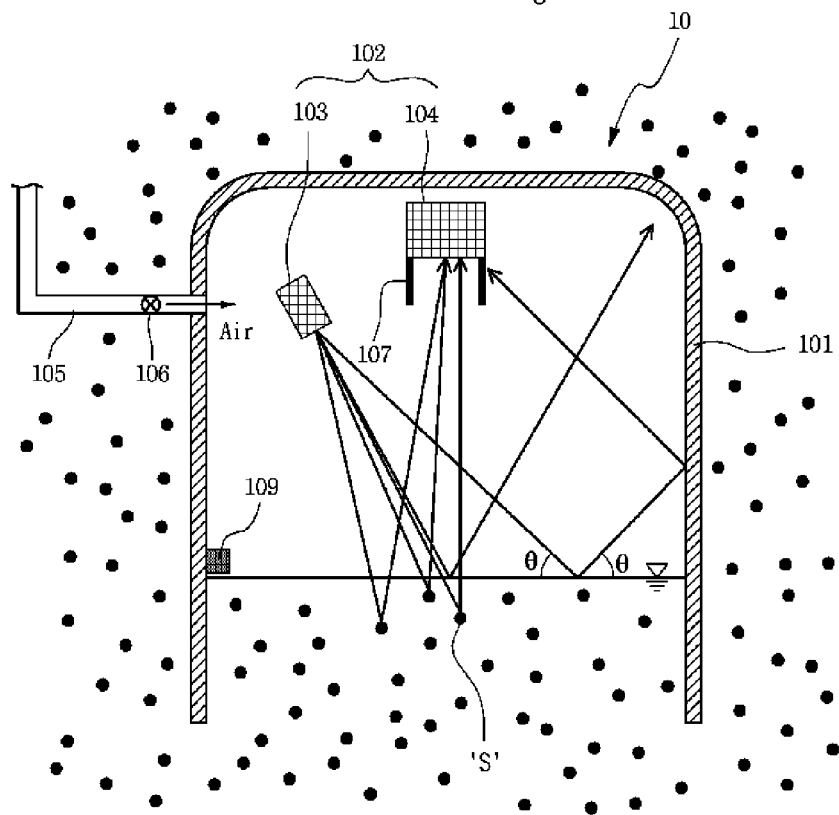
FIG. 3 is a sectional view of an embodiment of a sludge density sensing unit according to the present invention.

FIG. 3 is a sectional view of an embodiment of a sludge density sensing unit according to the present invention. Referring to FIG. 3, the density sensing unit 10 comprises a tube-shaped container 101 with the bottom open, a sensor installed as fixed in the container 101, a pressure maintaining means to maintain inside pressure of the container 101 by injecting air-like gas therein.

The container 101 is submerged in the wastewater treatment tank 1 as filled with gas. As a result, there is some space formed in the container 101 by the pressure of the gas, and water surface formed in lower part of the container 101 with a certain height.

The sensor 102 is an optical sensor including a light-emitting unit 103 which is fixed in the container 101 to emit light toward the water surface formed in the lower part of the container 101, and a light-receiving unit 104 which light emitted from the light-emitting unit 103 and reflected by sludge enters. The sensor 102 is electrically connected with a controller 20, which takes sludge density by amount of light which enters the light-receiving unit 104.

It is preferable for the light-emitting unit 103 to be installed as inclined by a certain angle against the light-receiving unit 104. It is for the purpose of minimizing the amount of the light entering the light-receiving unit 104 after being emitted from the light-emitting unit 103 and reflected from water surface, not by sludge (S).

To be more specific, when light emitted from the light-emitting unit 103 hits an interface like water surface, the light is reflected by the same angle with the incident angle. Therefore, if the light-emitting unit 103 and the light-receiving unit 104 are installed in parallel, light vertically emitted from the light-emitting unit 103 is highly possible to enter the light-receiving unit 104 after being reflected by water surface. Otherwise, when the light-emitting unit 103 and the light-receiving unit 104 are installed slantingly with a certain angle, the light which is slantingly emitted by the light-emitting unit 103 and reflected by water surface is considerably reduced for entering the light-receiving unit 104.

In addition, the light-receiving unit 104 can have a light shielding wall 107 extended downwards on the lower part thereof in order to prevent side-reflected light from entering.

The sensor 102 is preferably configured thus to minimize the light which is emitted from the light-emitting unit 103, reflected by water surface or the inner surface of the container 101, and enters the light-receiving unit 104; and to make the light reflected by sludge selectively enter the light-receiving unit 104.

The sensor 102 can comprise one of an LED, a photodiode, and the like. Besides, when the sensor 102 adopts infrared or ultraviolet wavelength light as its light source, the sensor can exclude influence of a foreign light. When the sensor takes a defusion-type bulb like a general LED or a halogen lamp as its light source, not only the reflection area of the light source by sludge increases, but also does the reflection area by the water surface, thereby increasing the possibility for the light reflected by the mere stirring of water surface to directly enter the light-receiving unit of a sensor. Otherwise, when the light source is a laser, its high permeability and uniform direction prevent signals from diffusing out which is caused by reflection on water surface. As a result, when the light source is an infrared or ultraviolet laser, it has an advantageous effect in that it decreases influence of a foreign light source and light diffusion caused by reflection of water surface, thereby taking exact sludge density. The present embodiment sets case that the sensor 102 takes an LED light source.

The container 101 is preferable to be or dark color like black in order to minimize the influence of outside light on the sensor 102. Moreover, the container 101 can have the inner surface coated with a material of low reflection rate or of non-reflection; or the container 101 itself can be made of such a material.

Meanwhile, because the gas in the container 101 is dissolved as time going by, the pressure in the container 101 gets lower. As a result, the water level rises and the measured value of the sludge density can differ even at the same density.

Therefore, it is preferable to maintain the pressure in the container 101 at a certain level by providing gas regularly or intermittently in the container 101 through a pressure maintaining means.

Such a pressure maintaining means can comprise a gas injection tube 105 connected with the container 101 as funneled, a valve 106 to open/close the gas injection tube 105, a gas supplying unit (not shown) to provide gas through the gas injection tube 105, wherein the gas supplying unit may comprise an air blower or an air pump.

In addition, the container 101 can have a water level sensor 109 installed on the inner surface thereof in order to control the opening/closing operation of the valve 106 by sensing the water level in the container 101. When the pressure in the container 101 gets lower and the water level goes up, the water level sensor 109 senses change in water level; the valve 106 gets opened; and gas is provided in the container 101, thereby increasing the pressure in the container 101 and lowering the water level down to a given level. When a water level sensor 109 is installed in the container 101 as described above, it is possible to not only maintain the proper water level in the container 101 but also prevent gas from being provided excessively in the container 101.

The water level sensor 109 can comprise one of various sensors common in the art: for example, a float water level indicator can be used to sense the water level and control the opening/closing operation of the valve 106.

The density sensing unit 10 described above operates as follows.

When the container 101 is put in the wastewater in the wastewater treatment tank 1 (Refer to FIG. 2) from above, the inside of the container 101 is filled with gas such as air and the gas pressure prevents the water from filling the container 101 and causes the water level to be kept at the lower part of the container 101.

Then, the light-emitting unit 103 of the sensor 102 emits light and the emitted light is reflected by hitting the water surface or particles of sludge (S) in the water. As explained above, since the light reflected by the water surface has the same angle of reflection with that of incidence, most of the light does not enter the light-receiving unit 104, but side-escapes or is shielded from entering the light-receiving unit 104 by the light shielding wall 107. Otherwise, when the light hits particles of sludge (S), it occurs diffused reflection, resulting in reflection by different angle with the incidence angle. At this time, the light only vertically reflected by particles of sludge (S) enters the light-receiving unit 104 escaping the light shielding wall 107 which is placed at the lower part of the light-receiving unit 104.

As wastewater has a lot of sedimented particles of sludge (S) therein, the amount of light that enters the light-receiving unit 104 by such diffused reflection increases; on the contrary, as wastewater has small amount of sedimented particles of sludge (S) therein, the amount of light entering the light-receiving unit 104 by such diffused reflection decreases. That is, the amount of light entering the light-receiving unit 104 is in proportion to the number of sludge particles.

The controller 20, therefore, can measure the sludge density according to the amount of light that enters the light-receiving unit 104.

Meanwhile, in case that the density sensing unit 10 is half immersed not whole as shown in FIG. 1, and in case that the density sensing unit 10 measures the sludge density moving along the elevating unit 30, various factors such as vibration of the elevating unit 30 or inflow of wastewater cause wastewater to shake. Such shaking of wastewater is transmitted to the water surface in the container 101, resulting in vibration thereof.

When there occurs vibration on the water surface in the container 101, the amount of light which is emitted from the light-emitting unit 103 and enters the light-receiving unit 104 changes, thereby causing not exact measurement of sludge density.

Figure 4:
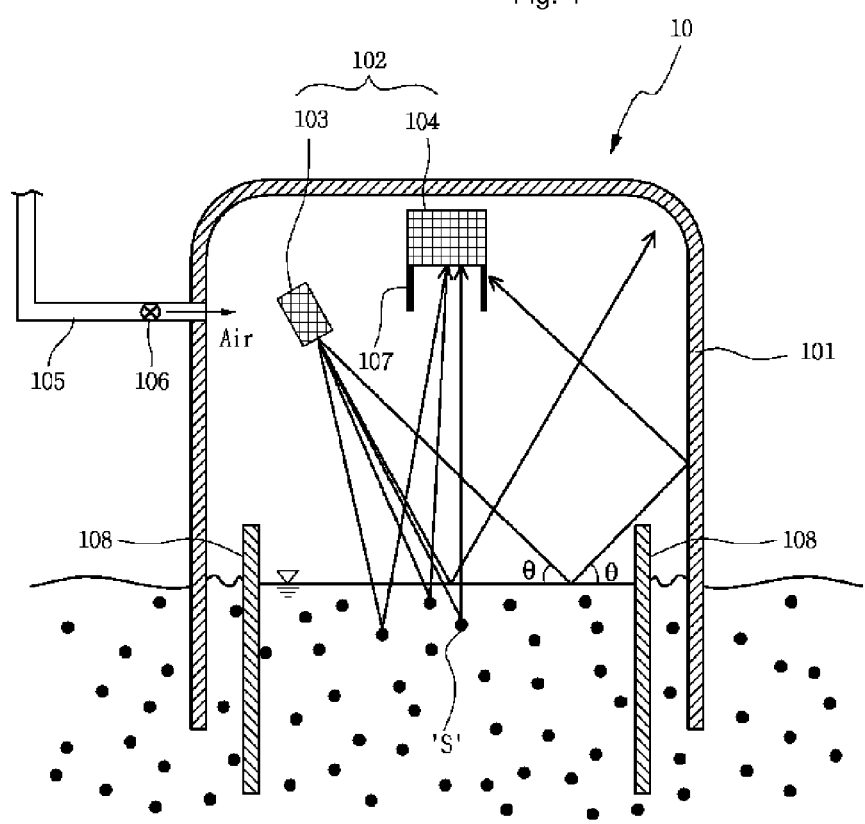
FIG. 4 is a sectional view of another embodiment of a sludge density sensing unit according to the present invention.

Therefore, as illustrated in another embodiment of the density sensing unit 10 in FIG. 4, the container 101 can have a vibration shielding plate 108 formed in the lower space therein as leaving space with the inner surface thereof, thereby minimizing the transmission of the vibration to the water surface therein.

According to the present invention, the light-emitting unit 103 and the light-receiving unit 104 of the density measuring sensor 102 are placed in the space in the container 101 without wastewater, thereby not directly contacting with wastewater, and not being contaminated by sludge.

Figure 5:
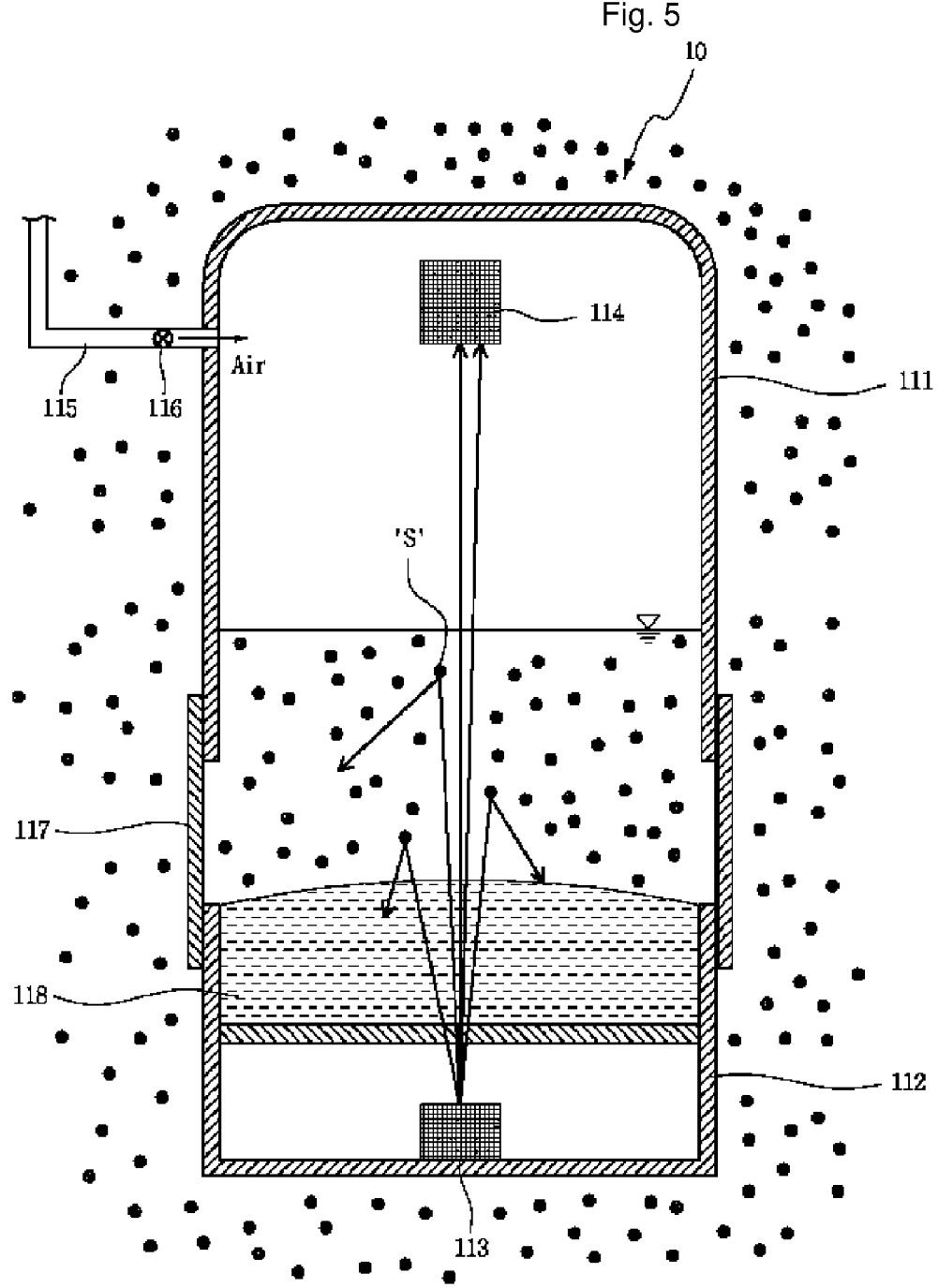
FIG. 5 is a sectional view of still another embodiment of a sludge density sensing unit according to the present invention.

FIG. 5 is a sectional view of still another embodiment of a sludge density sensing unit according to the present invention. Referring to FIG. 5, the density sensing unit 10 comprises an upper container 111 which is tube-shaped with the bottom open and submerged in wastewater as filled with gas therein and a lower container 112 which is combined with the upper container 111 as separated by a certain distance and is airtight therein by being closed all around thereof.

The lower container 112 has a light-emitting unit 113 installed at the lower space therein to emit light upwards; and the upper container 111 has a light-receiving unit 114 installed at the upper space therein to receive light emitted from the light-emitting unit 113.

And the upper part of the lower container 112 has an oil layer 118 formed with specific gravity of 1.6 bigger than that of water. The oil layer 118 is formed to expose the upper surface which is the path of light. Even if sludge particles (S) come close to the upper part of the oil layer 118, hydrophilic sludge particles do not adhere to hydrophobic oil layer 118. The density sensing unit 10, therefore, does not have to be cleansed.

Since the oil layer 118 has bigger specific gravity than water, openness of the whole upper part or some part thereof does not cause it to float on water, and the oil layer 118 remains on the upper part of the lower container 112.

The upper container 111 and the lower container 112 are linked by a plurality of bar-like coupling members 117 which are composed of a wire or a rigid body.

As for the upper container 111, as described in previous embodiments, therein are a pressure maintaining means installed, that is, a gas injection tube 115 and a gas supplying unit (not shown) in order to maintain the uniform pressure by supplying gas therein.

The density sensing unit 10 in this embodiment operates as follows.

Almost vertically emitted light from the light-emitting unit 113 proceeds toward the light-receiving unit 114. At this time, if there are sludge particles (S) in wastewater between the upper container 111 and the lower container 112, some of the emitted light from the light-emitting unit 113 is reflected by hitting the sludge particles (S) and does not enter the light-receiving unit 114. In other words, as there are a lot of sludge particles (S), that is, as the sludge density increases, the amount of light reflected by sludge increases and the amount of light entering the light-receiving unit 114 decreases.

To sum up, the amount of light entering the light-receiving unit 114 is in inverse proportion to the number of sludge particles; and the controller 20 can thus measure sludge density according to the amount of light entering the light-receiving unit 114.

Figure 6:
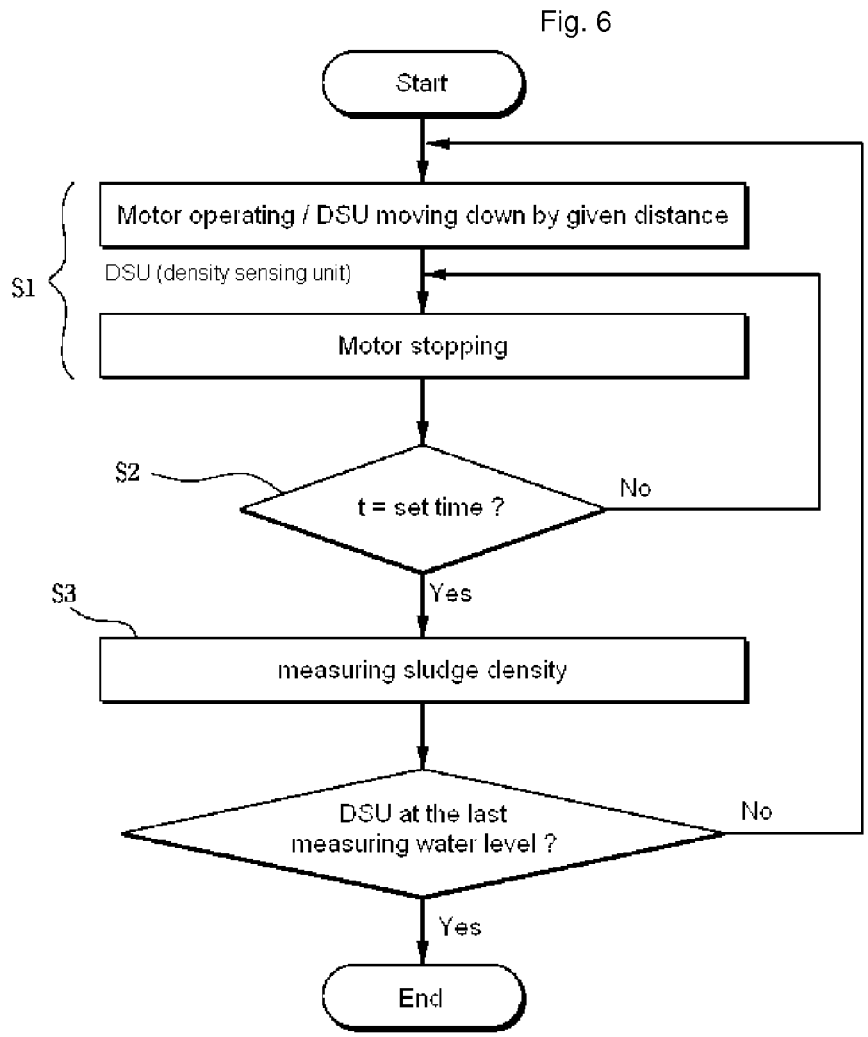
FIG. 6 is a flowchart showing an embodiment of a method for sensing sludge density according to the present invention.

FIG. 6 is a flowchart showing an embodiment of a method for sensing sludge density according to the present invention. Referring to FIGS. 2 and 6, the method for sensing the sludge density by use of the density sensing unit of the present invention is as follows.

After placing the density sensing unit 10 at the upper part of the wastewater treatment tank 1 and applying a control signal to the motor 35 of the elevating unit 30, the upper pulley 32 gets to rotate, and in turn the belt 34 revolves, thereby making the density sensing unit 10 move down by a given distance.

When the density sensing unit 10 moves down by a given distance, for example, by 30 cm, the motor 35 stops operating and the density sensing unit 10 is suspended at the spot (S1).

Next, the density sensing unit 10 does not measure density at all for a set time (t); or the controller 20 stands by ignoring the density sensing signal (S2).

After the set time (t) is over, the density sensing unit 10 begins to carry out measuring density; and the controller 20 takes and stores the sludge density at this water level (S3).

After the taking the sludge density at the water level is completed, the control signal is applied again on the motor 35 of the elevating unit 30, thereby making the motor 35 operate and making the density sensing unit 10 move down by a given distance to take the sludge density at the next measuring spot.

The density sensing apparatus measures and stores the sludge density by each water level in the wastewater treatment tank 1, performing such a process over again as described above until the density sensing unit 10 arrives at the last measuring water level. When the taken sludge density at a certain water level becomes a set value, the apparatus performs a proper process like operating the discharging pump 5 to discharge sludge.

When taking the density at each water level by moving the density sensing unit 10 by a given distance, it is preferable to maintain the uniform water level which is formed at the lower part of the container 101 of the density sensing unit 10 by supplying gas such as air regularly or intermittently therein.

Meanwhile, when taking sludge density at each water level as the density sensing unit 10 moving down by one step with a given distance, the density sensing unit 10 stands by for a set time (t), not measuring the sludge density as soon as it reaches the set water level. The reason is for the density sensing unit 10 to take stable measured value after the vibration of the water in the lower part of the container 101 (Refer to FIG. 3) gets still, wherein the vibration occurs when the density sensing unit 10 moving.

To be more specific, while the density sensing unit 10 is moving down by the operation of the elevating unit 30, the container 101 of the density sensing unit 10 (Refer to FIG. 3) is made to vibrate by the vibration generated by the operating source of the elevating unit 30, thereby causing the water in the lower part of the container 101 to shake.

If the water in the lower part of the container 101 comes to shake, the light emitted from the light-emitting unit 103 of the sensor 102 hits the water surface and enters the light-receiving unit 104, which prevents the sensor from measuring the density exactly.

Figure 7:
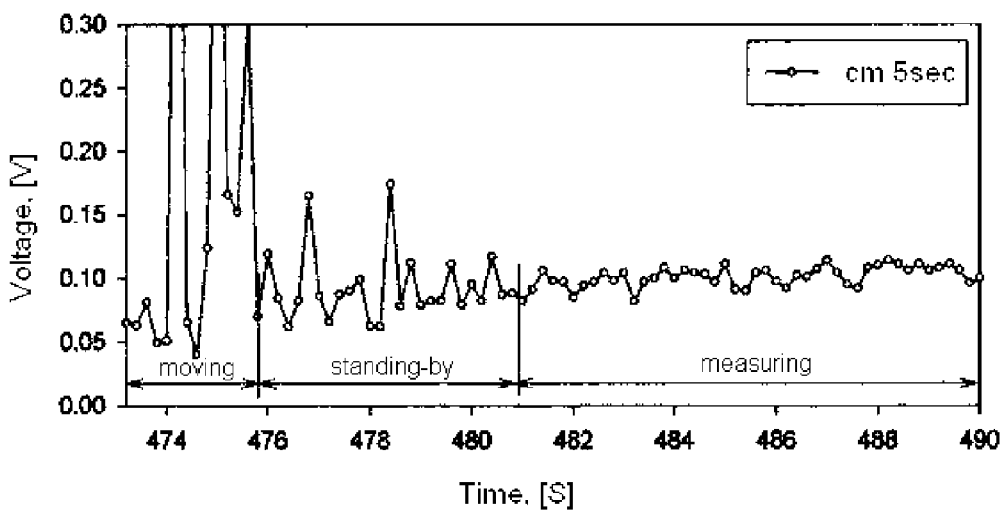
FIG. 7 is a diagram illustrating signals which enter the light-receiving unit of another embodiment of an apparatus for sensing sludge density according to the present invention.

FIG. 7 is a diagram illustrating signals which enter the light-receiving unit of another embodiment of an apparatus for sensing sludge density according to the present invention. Referring to FIG. 7, while the density sensing unit 10 is initially moving, the vibration on water surface is so big that the amount of the light entering the light-receiving unit 104 is quite varying.

When the density sensing unit 10 moves by a given distance and stops, the vibration gets still and the measured signal becomes stable.

After a set time (5 seconds in the FIG. 7) runs out from the time the density sensing unit 10 stops, the water surface becomes still and the measured signal shows stable enough value. Then the controller 20 takes average value from inputted signals after the end of the set time (t) to calculate the sludge density, which is more accurate.

Since the density sensing unit 10 measures sludge density after moving by a given distance step by step, and then having a stabilization stage while standing by for a certain time, thereby making it accurate to measure sludge density by water level of the wastewater treatment tank 1 and facilitating processes by grasping the whole state of sludge density in the wastewater treatment tank 1 in real time.

Although the present invention has been described with reference to several preferred embodiments, the description is illustrative of the invention and is not to be construed as limiting the invention. Various modifications and variations may occur to those skilled in the art, without departing from the scope of the invention as defined by the appended claims.

The invention claimed is:

1. An apparatus for sensing precipitation density of sludge in a wastewater treatment tank, comprising:
   a container which is tube-shaped with a bottom thereof open and submerged in wastewater as filled with gas therein; and
   a sensor which is installed in a space in the container, and senses sludge density as not directly contacting with wastewater;
   wherein said sensor includes a light-emitting unit to emit light toward the water surface formed in the lower part of said container; and
   a light-receiving unit for light emitted from said light-emitting unit and reflected by hitting sludge under said water surface to enter,
   wherein said light-receiving unit has a light shielding wall extended downwards in order to shield side reflected light from entering.

2. The apparatus of claim 1, further comprising a controller which is electrically connected with said sensor and measures sludge density by the amount of light entering said sensor.

3. The apparatus of claim 1, further comprising:
an elevating unit to move said sensor up and down.

4. The apparatus of claim 3, wherein said elevating unit includes
- a guide frame installed vertically in said wastewater treatment tank;
- a upper pulley and a lower pulley installed at the upper part and the lower part of said guide frame respectively;
- a belt located on said upper pulley and said lower pulley with tension given thereon;
- a connection piece to connect said belt with said density sensing unit;
- a motor to rotate said upper pulley to desired degree.

5. The apparatus of claim 3, wherein said density sensing unit takes sludge density as moving by a given distance step by step from the upper part to the lower part in said wastewater treatment tank.

6. The apparatus of claim 1, further comprising a pressure maintaining means to inject gas into said container in order to maintain uniform pressure in the space of said container.

7. The apparatus of claim 6, wherein said pressure maintaining means includes a gas injection tube which is connected with said container as funneled;
- a valve to open/close said gas injection tube; and
- a gas supplying unit to supply gas through said gas injection tube.

8. The apparatus of claim 7, wherein said pressure maintaining means further includes a water level sensor to control opening/closing operation of said valve by sensing water level in said container.

9. The apparatus of claim 6, further comprising a vibrating shielding plate which is formed in the lower space in said container as leaving space with the inner surface of said container, thereby preventing vibration on surface of water in said container caused by shaking of wastewater.

10. The apparatus of claim 1, wherein said light-emitting unit is installed as inclined by a given angle against said light-receiving unit.

11. The apparatus of claim 1, wherein said container includes a upper container which is tube-shaped with a bottom thereof open and submerged in wastewater as filled with gas therein, and
- a lower container which is combined with said upper container as separated by a certain distance and is airtight therein by being closed all around thereof; and
said sensor includes
- a light-emitting unit installed in the space of said lower container to emit light upwards, and
- a light-receiving unit installed in the space of said upper container to receive the light emitted from said light-emitting unit.

12. The apparatus of claim 11, further comprising a pressure maintaining means to inject gas into said upper container in order to maintain uniform pressure in the space of said upper container.

13. The apparatus of claim 12, wherein said pressure maintaining means includes a gas injection tube which is connected with said upper container as funneled;
- a valve to open/close said gas injection tube; and
- a gas supplying unit to supply gas through said gas injection tube.

14. The apparatus of claim 13, wherein said pressure maintaining means further includes a water level sensor to control opening/closing operation of said valve by sensing water level in said upper container.

15. The apparatus of claim 11, further comprising a plurality of coupling members to link said upper container with said lower container.

16. The apparatus of claim 11, wherein said lower container has an oil layer formed in the upper part thereof, the specific gravity of the oil layer being bigger than that of water, and the upper surface of the oil layer being exposed outwards.

17. The apparatus of claim 1, wherein said container is made of an opaque material in order to prevent any light from entering.

18. A method for sensing precipitation density of sludge in a wastewater treatment tank, comprising:
- moving in which a density sensing unit is allowed to move by a given distance from the upper part to the lower part in a wastewater treatment tank and to stop at a measuring spot in said wastewater treatment tank;
- stabilizing in which said density sensing unit stands by for a set time after the time said density sensing unit stops at said measuring spot; and
- measuring in which said density sensing unit measures sludge density at the water level of said measuring spot after said set time is over,
- wherein said moving, stabilizing, and measuring are sequentially repeated until said density sensing unit reaches the last measuring spot in the lower part of said wastewater treatment tank.

19. The method of claim 18, wherein said density sensing unit is regularly or intermittently supplied with gas in order to maintain uniform pressure therein while said density sensing unit takes sludge density as moving from the upper part to the lower part in a wastewater treatment tank.

* * * * *

UNITED STATES PATENT AND TRADEMARK OFFICE
CERTIFICATE OF CORRECTION

PATENT NO.        : 8,379,211 B2                                    Page 1 of 1
APPLICATION NO. : 12/514858
DATED             : February 19, 2013
INVENTOR(S)       : Kwak et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 921 days.

Signed and Sealed this
First Day of September, 2015

Michelle K. Lee
*Director of the United States Patent and Trademark Office*